United States Patent [19]

Hodge et al.

[11] Patent Number: 5,423,338
[45] Date of Patent: Jun. 13, 1995

[54] DENTAL FLOSSING TOOL

[76] Inventors: Rex A. Hodge, 5101 Bassett Way, Sacramento, Calif. 95823; Lyn M. Cowgill, 6010 Tall Brave Ct., Citrus Heights, Calif. 95621

[21] Appl. No.: 212,192

[22] Filed: Mar. 8, 1994

[51] Int. Cl.$^6$ .............................................. A61C 15/00
[52] U.S. Cl. ..................................... 132/324; 132/326; 132/327; 132/325
[58] Field of Search ................ 132/323, 324, 325, 326, 132/327

[56] References Cited

U.S. PATENT DOCUMENTS

| D. 279,826 | 7/1985 | Schindler | D28/64 |
|---|---|---|---|
| 844,181 | 2/1907 | Overbaugh | 132/324 |
| 2,098,610 | 11/1937 | Bluhm | 132/325 |
| 2,544,276 | 3/1951 | Ness | 132/326 |
| 3,746,017 | 7/1973 | Casselman | 132/92 |
| 3,882,879 | 5/1975 | Lucas | 132/326 |
| 3,886,956 | 6/1975 | Cash | 132/325 |
| 4,206,774 | 6/1980 | Griparis | 132/92 |
| 4,253,477 | 3/1981 | Eichman | 132/91 |
| 4,495,957 | 1/1985 | Beggs et al. | 132/92 |
| 4,556,074 | 12/1985 | Morin et al. | 132/92 |
| 4,615,349 | 10/1986 | Kukuruzinski | 132/91 |
| 5,183,065 | 2/1993 | Mason | 132/325 X |
| 5,207,773 | 5/1993 | Henderson | 132/322 |
| 5,251,651 | 10/1993 | Mason | 132/326 |
| 5,261,430 | 11/1993 | Mochel | 132/322 |

FOREIGN PATENT DOCUMENTS

| 2237203 | 5/1991 | United Kingdom | 132/324 |
|---|---|---|---|
| 9107143 | 5/1991 | WIPO | 132/324 |

*Primary Examiner*—Nicholas D. Lucchesi

[57] ABSTRACT

This invention is substantially a device for properly orienting and securing dental floss for the purpose of cleaning the regions between the teeth in a convenient manner. Floss resides in a storage cavity such as can be located in the handle of the device. The floss is routed from the cavity through a system of grooves to a U-shaped member which places the floss between the teeth. A locking mechanism removes slack from the floss and engages a taunt grip on the floss. The aforementioned locking mechanism is readily disengaged to allow advancement to a new section of floss. A compliant sealing member is attached to the locking mechanism to prevent fluids from entering the floss chamber.

5 Claims, 4 Drawing Sheets

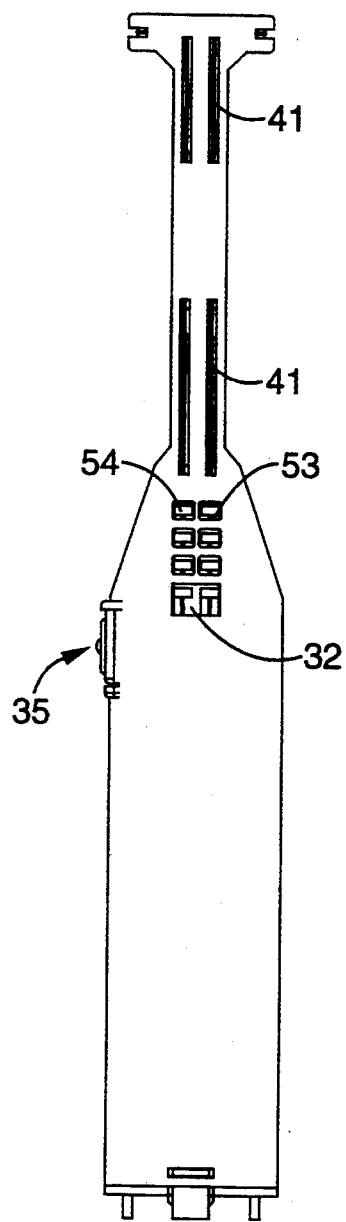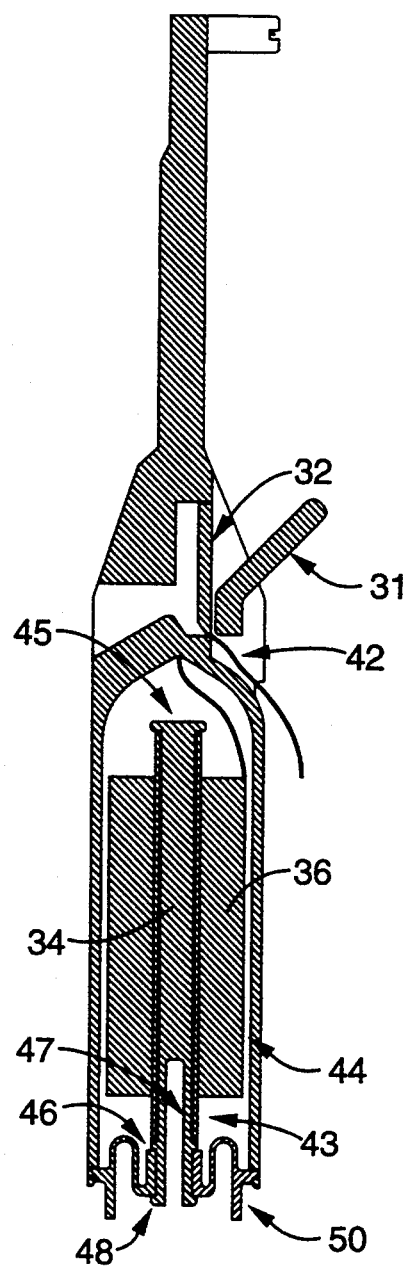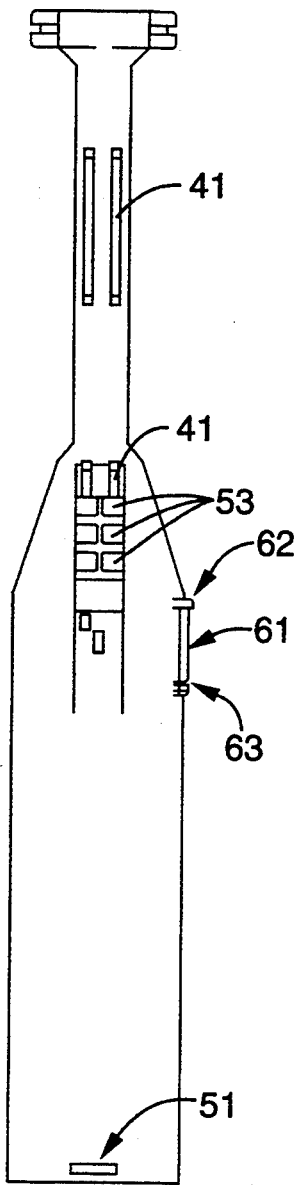
FIG. – 6  FIG. – 7  FIG. – 8
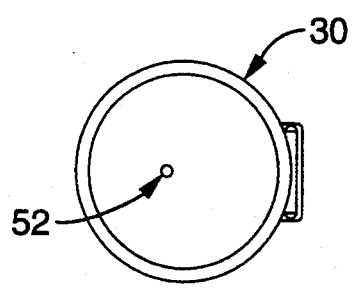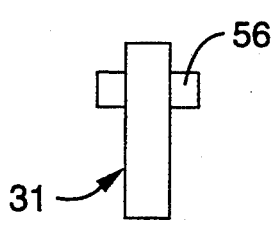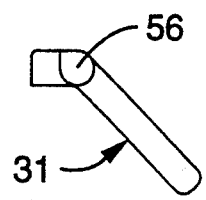
FIG. – 9  FIG. – 10  FIG. – 11

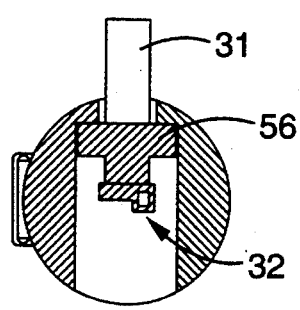
FIG. – 13
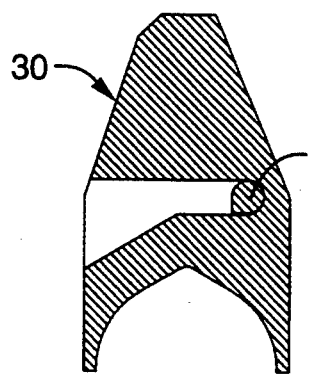
FIG. – 14
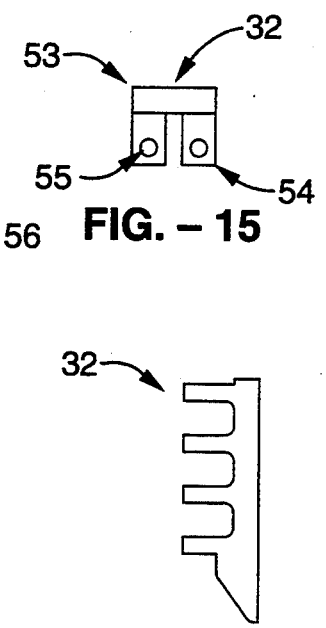
FIG. – 15
FIG. – 16
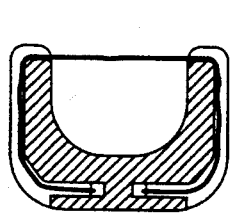
FIG. – 17
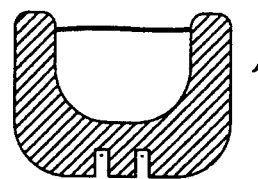
FIG. – 18
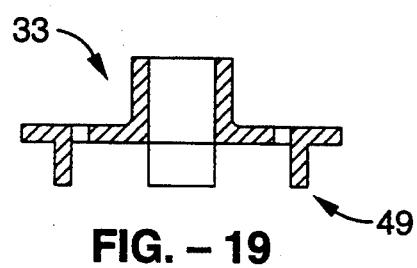
FIG. – 19
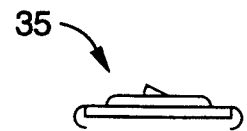
FIG. – 20
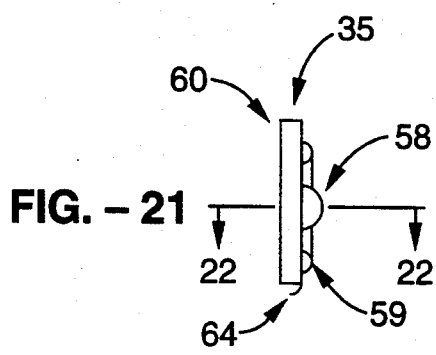
FIG. – 21
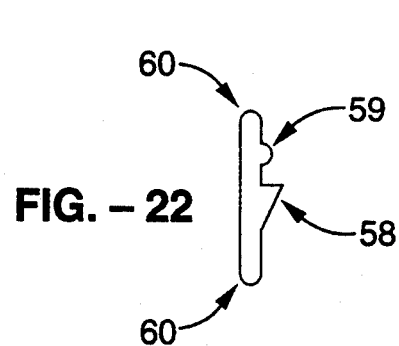
FIG. – 22

DENTAL FLOSSING TOOL

BACKGROUND—FIELD OF THE INVENTION

This invention relates to dental floss holding and positioning devices.

BACKGROUND—DESCRIPTION OF PRIOR ART

The typical daily techniques used to maintain good oral hygiene and healthy teeth and gums include brushing and flossing. Brushing, especially with the aid of fluoride, is an effective method of cleaning the exposed areas of the teeth. Areas between the teeth and especially between the teeth and just under the gum line, are not adequately serviced by brushing. The act of flossing will clean these areas, reducing the chances of tooth decay. Flossing will also massage, and thereby, strengthen the gums.

Flossing is traditionally performed by wrapping the ends of a small section of floss about the fingers of both hands and inserting the fingers into the mouth. Many individuals find this process awkward and thus refuse to floss. Other individuals have physical impairments, such as arthritis, which make this task particularly arduous.

In the prior art there are many attempts to produce a device capable of simplifying the flossing process by gripping the floss in a holder such that the device may be held on outside the mouth and such that a high degree of manual dexterity is not required to both grip and position the floss. Previous floss holding devices, however, have certain disadvantages which have prevented them from being put into general use.

A major category of previous flossing devices is the disposable floss holder. Typically, as in U.S. Pat. No. Des. 279,826 to Schindler (1985), a short segment of floss is bonded to a small frame, usually by means of molding the frame about the floss. These devices are expensive and wasteful as the frame material must be disposed of with each flossing. Often the floss is held in line with the axis of the frame structure, which is an awkward orientation for flossing the back teeth. As these are disposable units, many of these devices have small handles to minimize material costs. These small handles do not have sufficient rigidity, nor a large enough gripping surface for convenient flossing. Some flossing devices have overcome the holding and positioning problems of this category of flossing tools by configuring the floss holding structure as a cartridge which attaches to a longer lasting and substantially larger handle as in U.S. Pat. No. 5,261,430 to Mochel (1993). The floss is held in a more convenient orientation perpendicular to the axis of the handle which allows for better access to the back teeth. U.S. Pat. No. 4,253,477 to Eichman (1981) and others use a variation on this theme by bonding small beads to each end of a small segment of floss and holding each bead in the reusable handle. U.S. Pat. No. 4,615,349 to Kukuruzinski (1986) achieves the proper flossing orientation by stapling floss into a relatively compliant member. Placing staples into the mouth may not be prudent in that some manufacturing defect may allow the staples to be released while in the mouth. All of these types of flossing devices, whether or not the floss is conveniently oriented, are still limited by the expense and wastefulness of disposing the frame structure or other floss gripping component with each flossing.

A common method of gripping floss, as in U.S. Pat. No. 4,556,074 to Morin et al. (1985), is to provide one or more posts around which the floss can be repeatedly wrapped to develop sufficient friction to resist the significant forces involved in flossing. This method is time consuming and awkward as the floss must be pulled extremely taunt while performing the repeated encircling of the post members.

Another reoccurring approach is to wedge the floss between the threads of a two component device, as represented in U.S. Pat. No. 4,206,774 to Griparis (1980). In this scheme the device is disassembled, the floss is advanced and placed between the threaded regions of the two parts and the device is reassembled by re-engaging the two threads and rotating one or both parts until the floss is securely locked in place. This approach is again awkward and time consuming. Additionally, the floss is often disfigured by the sliding of the threads during the rotation of the components.

A technique using a rotating dispensing cylinder and a rotating collecting cylinder has been suggested in both manual rotation and motor driven forms as in U.S. Pat. Nos. 3,746,017 to Casselman (1973) and 5,207,773 to Henderson (1993) respectively. With this configuration two cylindrical spools rotate in a synchronous fashion. The floss leaves one spool to be routed to the region of the device in contact with the teeth and from this region to the other spool. Tension is typically maintained by the equal and opposite rotation of the two cylinders. This technique requires a complex and expensive device. Additionally, the storage of the spent floss in the device is not sanitary. Although it is occasionally suggested that the spent floss may in some manner be sanitized, this would be an additional expense and may be unreliable.

There also exists in the prior art, tools which require the user to force one part of the device against another part of the device with the floss between, thereby effecting a clamping action on the floss as in U.S. Pat. No. 4,495,957 to Beggs et al. (1985). These devices can be made inexpensively but require a that constant force be applied to the two components by the hand of the user while at the same time placing the device into the mouth and forcing the clamped floss between the teeth. Supplying these two forces simultaneously requires strength and dexterity.

Floss holding devices in the prior art typically do not have a provision for sealing the floss containing compartment from fluid to which the device may be exposed. One device, U.S. Pat. No. 5,251,651 to Mason (1993) contains a seal to protect the stored floss. However, this unit merely grips one end of the floss and, thus, does not allow the user to position the floss solely with the device itself therefore failing to make the flossing process significantly more convenient.

OBJECTS AND ADVANTAGES

It is the object of this invention to define a floss holding tool which overcomes many of the problems encountered by the prior art. It is the object of this invention to overcome these problems with a device possessing the following advantages:

(a) a floss holding device where the frame structure and the floss gripping components are reusable thereby reducing waste and cost while allowing for an increase in strength and rigidity;

(b) a floss holding device which is easy to hold and manipulate by the hand of the user;

(c) a floss holding device where the floss is held in an orientation convenient for accessing all of the teeth, including the back teeth;

(d) a floss holding device with no loose components in the region to be inserted into the mouth to prevent a portion of the device from breaking free and being inadvertently swallowed;

(e) a floss holding device where the floss is readily advanced to a new section and readily secured for flossing in a convenient manner requiting neither undue strength nor extraordinary manual dexterity;

(f) a floss holding device which remains sanitary by avoiding the storage of spent floss in an enclosed cavity;

(g) a floss holding device which is amiable to low cost production by using components which are readily mass produced in an assembly which is suitable for rapid production;

(h) a floss holding device where the floss is gripped by the device upon the enactment of a simple single-action motion which locks the floss into place such that the user need not be further involved in the holding or gripping of the floss itself;

(i) a floss holding device which contains a seal to protect the stored floss from fluids to which the device may be exposed.

Additionally, it is the object of this invention to introduce a floss holding device wherein a fluid management system provides for rapid vaporization of fluids by sealing off the floss storage compartment, by venting the floss storage compartment and by exposing the floss to the air by way of a series of grooves which lead from the floss storage compartment to the locking mechanism, to the region where contact with the teeth occurs and back to the locking mechanism.

It is also the object of this invention to accomplish the gripping of the floss through the use of a unique mechanism which uses a lever to displace a carriage suspended by the floss into a set of holes in the body of the device and thereby both remove slack from the floss and lock it into place. It is further the object of this invention to define a device where the previously mentioned locking mechanism can be readily disengaged by moving the lever into the unlocked position.

Still more objects and advantages will become apparent from a consideration of the ensuing description and drawings.

BRIEF DESCRIPTION OF THE DRAWINGS

In the drawings, like numerals refer to like features.

FIG. 6 shows the back view of device including a view of the locking carriage feet in position within the locking holes in the body.

FIG. 7 is a sectional view taken along line 7—7 in FIG. 2.

FIG. 8 is the front view of the body alone without the other components.

FIG. 9 is the bottom view of the body alone without the other components.

FIG. 10 is the top view of the lever.

FIG. 11 is the side view of the lever.

FIG. 13 is a sectional view taken along line 13—13 in FIG. 2.

FIG. 14 is a sectional view taken along line 14-14 in FIG. 2.

FIG. 15 shows the top view of the locking carriage.

FIG. 16 shows the side view of the locking carriage.

FIG. 17 is a sectional view taken along line 17—17 in FIG. 2.

FIG. 18 is a sectional view taken along line 18—18 in FIG. 2.

FIG. 19 is a sectional view taken along line 19—19 in FIG. 1 selectively showing only the cap and no other component.

FIG. 20 shows the top view of the cutter.

FIG. 21 shows the front view of the cutter.

FIG. 22 is a sectional view taken along line 22—22 in FIG. 21.

DETAILED DESCRIPTION OF THE PREFERRED EMBODIMENTS

Figures 1, 2, 3:
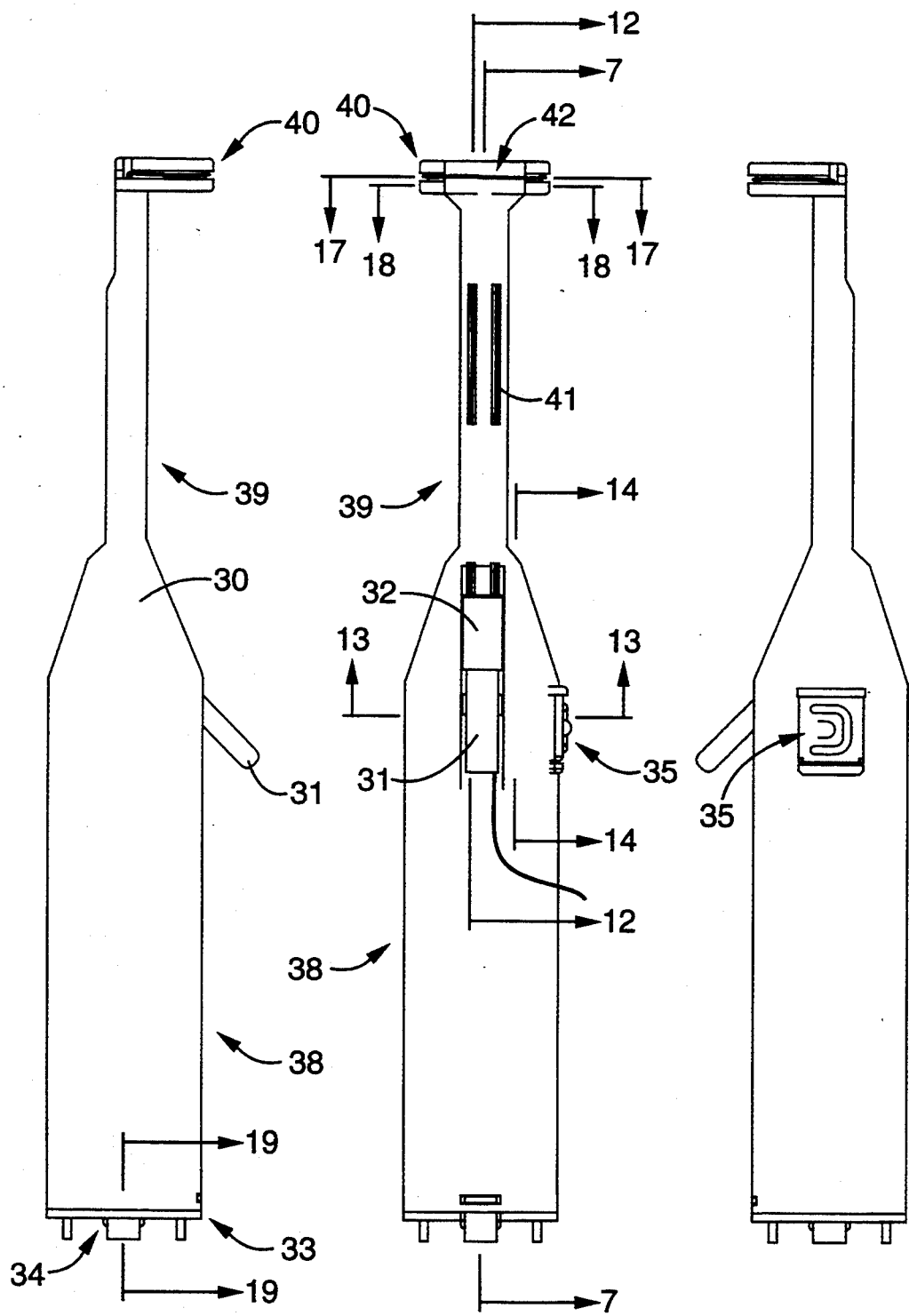
FIG. 1 shows a side view of the device including the handle, the shaft and a side view of the U-shaped floss placement region.
FIG. 2 shows the front of the device including grooves on the shaft, the lever and locking carriage.
FIG. 3 shows the side opposite the side in FIG. 1 and features the cutting device.

The description herein is merely the preferred embodiment of this device. Once this description is presented, there are a multitude of variations of this device which would be apparent to one skilled in the art and which would still fall within the boundaries of the claims presented in this patent.

As illustrated in FIGS. 1–8, the dental flossing tool described herein consists of a central body 30 and seven other components: a lever 31, a locking carriage 32, a cap 33, a spool rod 34, a cutter 35, a spool of floss 36 and a seal 37.

The body itself is primarily composed of a handle 38, a shaft 39 and a U-shaped floss placement region 40. The handle 38 is shaped for a comfortable grip within one hand. The shaft 39 has a small cross-section to appear similar to a toothbrush and thus be an object which the user will feel comfortable placing in the mouth. The U-shaped region 40 is also kept at a low profile while possessing sufficient length to place the floss below the gum line. The U-shaped region 40 is perpendicular to the shaft 39 to best orient the floss. When flossing the front teeth the shaft 39 is held parallel to the mouth. When flossing the back teeth the shaft 39 is held perpendicular to the mouth. In both cases the floss is held by the U-shaped region 40 in the correct position for insertion between the teeth in that area of the mouth.

The shaft 39 and U-shaped region 40 have a network of grooves 41. The floss 42 is routed through the device using these grooves 41. A spool of floss 36 is contained within a cavity in the handle 38 of the body 30 as shown in FIG. 7. The spool of floss 36 is of a commercially available configuration sold in plastic boxes in retail stores or used in dispensers in dental offices for use by the dentist or hygienists. The spool 36 actually consists of two parts, a small plastic tube 43 about which is wound a roll of 200 yards of dental floss 44. Unwaxed dental floss is used in this device to prevent wax buildup on comers of the device when the floss 42 is required to negotiate a turn. Dental studies have shown little or no difference between the cleaning and massaging characteristics of waxed and unwaxed dental floss.

The tube 43 of the spool of floss 44 is mounted on the floss spool rod 34. When the floss 42 is pulled through the device, the floss 42 may unwind by simply peeling off the spool 36 in a circular pattern which requires no rotation of the spool 36. This device, however, does allow the spool 36 to spin about the rod 34 should the floss 42 be tightly wound in a certain region where it may be beneficial for the spool 36 to rotate to a new position where the floss 42 is more readily pulled towards the shaft 39. The central tube 43 of the spool 36 is constrained to remain on the rod 34 by a disk 45 on one end of the rod 34 and retaining bumps 46 on the other end. A circular disk 45 is used to keep the spool 36 from coming off the top end of the rod 34 in order to prevent the floss 42 from catching on a corner as it is pulled off of the spool 36 and pulled towards the shaft 39. Fingers 47 extend front the rod 34 which are sized in section and length such that they can be bent inward when the spool 36 is assembled onto the rod 34. Once the spool 36 passes the retaining bumps 46 the fingers snap back into place, locking the spool 36 onto the rod 34 while still allowing the spool 36 to rotate.

Figure 5:
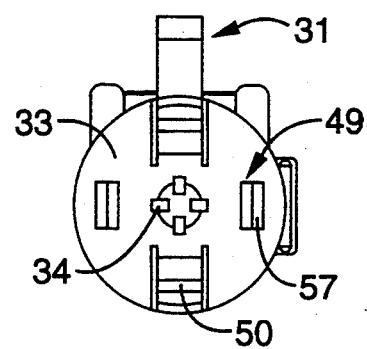
FIG. 5 shows the bottom view including the cap and the feet of the spool shaft.

This same scheme is used to secure the rod 34 to the cap 33. The same fingers 47 used above have an additional set of retaining bumps 48 which are pressed inward when the cap 33 is pressed onto the rod 34 during assembly. The fingers 47 then map back into place locking the cap 33 between the two sets of retaining bumps 46, 48. The cap 33 is held onto the handle 38 by another snap-fit joint. The cap 33 rests on four feet, two of which are stationary 49 as seen in FIG. 19 and two of which are mobile 50 as seen in FIG. 7. The mobile feet 50 are on a cantilevered section as seen in FIG. 5. This cantilevered section is curved as seen in FIG. 7 to increase the length of the cantilever and thus increase the flexibility of the mobile feet 50. The two mobile feet 50 can be squeezed together to place the cap 33 within the handle 38. The mobile feet 50 will then snap back to their original shape and thus be retained in the handle 38 as there are holes 51 in the handle 38 to receive protrusions in the mobile feet 50 as shown in FIGS. 7 and 8.

The floss 42 is routed from the spool 36 out of the floss cavity by a small passage 52. This small passage 52 positions the floss for the locking carriage 32 as shown in FIG. 12. The floss 42 passes through the locking mechanism and is routed through the shaft 39 and the U-shaped region 40 and then back through the shaft 39 through the grooves 41. The floss 42 then passes back through the locking mechanism and out of the device.

The heart of this device is the locking mechanism which is composed of three parts: the lever 31, the locking carriage 32 and a series of holes 53 in the body 30 as seen in FIGS. 7 and 8.

The locking carriage 32, shown in FIGS. 15 and 16, consists of a rectangular plate 53 from which two rows of four feet 54 each extend. Each row of feet 54 has a hole 55 which passes through it. As shown in FIG. 12b, the floss 42 passes through one row of these holes 55 when routed through the locking mechanism from the floss storage cavity to the shaft 39. The floss 42 then passes back through the second row of holes 55 on the second row of feet 54 on the way from the shaft 39 to exit the device at the top end of the handle 38. The locking mechanism will thus lock both the incoming and outgoing ends of the floss 42.

When in the unlocked position, as shown in FIG. 12b, the floss passes straight through the carriage without interference. The floss 42 can thus be easily pulled by the user to advance the floss 42 to a clean and unused section. In the locked position, however, the floss 42 is prevented from movement and, in fact, held under tension. This is accomplished by forcing the feet of the carriage into a set of holes 53 in the body 30. These holes 53 are seen in FIG. 8. When the feet 54 are forced into the holes 53 in the body the floss 42 moves from a straight path to a twisting path as it is forced to make several turns around each of the feet 54 and each of the walls separating the holes 53 in the body as shown in FIG. 12a.

Figure 12A:
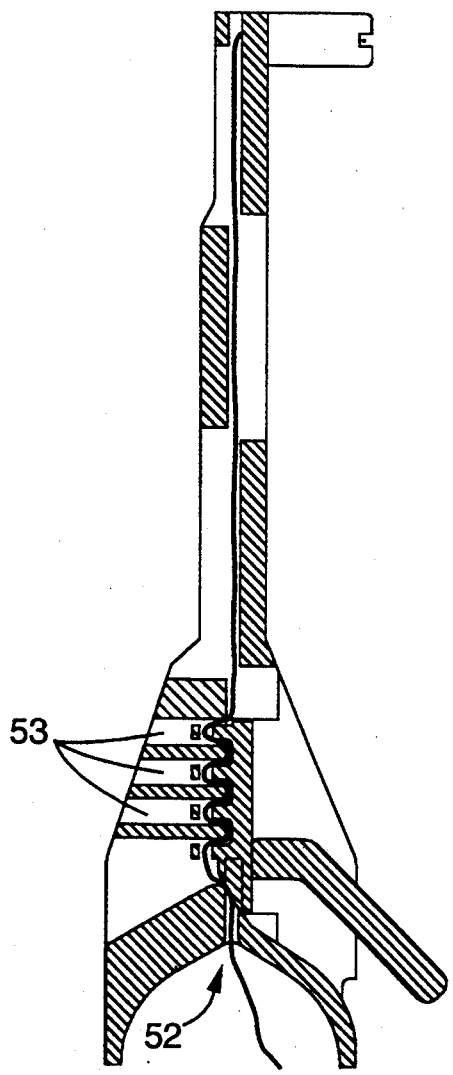
FIG. 12a and 12b are sectional views taken along line 12—12 in FIG. 2 with the locking mechanism engaged and disengaged respectively.
Figure 12B:
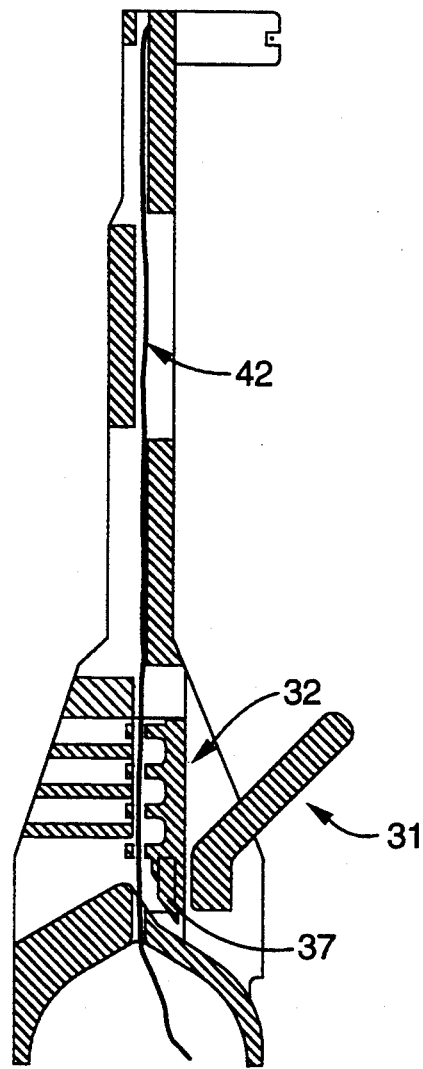
Figure 4:
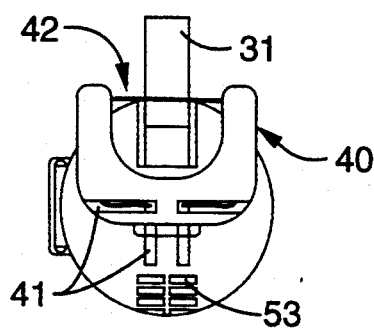
FIG. 4 shows the top view of the device including the U-shaped region and the locking holes in the body.

The locked configuration of FIG. 12a has a longer path length for the floss 42. As the feet 54 of the carriage 32 are pressed into the holes 53 in the body 30, slack is thus removed from the floss 42. Furthermore, the floss 42 is now constrained from movement once it is in the locked position as the torturous path around the feet 54 of the carriage 32 and the walls between the holes 53 develops significant friction. In fact, prototype testing of this device shows that the resistive force locks the floss 42 in place even under high flossing loads.

The carriage 32 feet 54 are forced into the holes 53 in the 30 by the lever 31. The lever 31 is an angled plate with a special pin 56 attached to it as shown in FIGS. 10 and 11. The pin 56 resides in a slot in the body 30 as shown in FIG. 14. One corner of the pin 56 is brought to a point, generating two flat sides in one quadrant of an otherwise circular pin. This has the effect of limiting the rotation of the pin 56. The pin 56 is allowed to rotate until one side of the corner comes into contact with the wall of the slot in the body 30. The pin 56 is also allowed to rotate in the other direction only until the other side of the corner comes into contact with the other wall of the slot, at which time it is constrained to stop. One of these limits is the locked position and the other is the unlocked position. The user, thus, merely moves the lever 31 from one position to the other to lock or unlock the mechanism without having to consider how far to move the lever 31. Rotation of the lever 31 occurs about the center of the pin 56. When the lever 31 is in the unlocked position shown in FIG. 12b the carriage 32 is allowed to move until it rests on the side of the lever 31 facing the side of the carriage 32. When the lever 31 is in the locked position shown in FIG. 12a a different side of the lever 31 is in contact with the carriage 32. This new side of the lever is further away from the center of the pin 56. As a result, the carriage 32 is constrained to be further away from the pin 56 and thus the feet 54 of the carriage 32 are constrained to be within the holes 53 of the body 30. The floss 42 is thus locked as previously explained.

In addition to the limits on the rotation of the lever 31 imposed by the corner of the pin, another feedback method exists to inform the user when the lever 31 is in the locked or unlocked position as the lever 31 is moved. As the lever 31 rotates, a rounded corner of the lever between the two surfaces that come into contact with the carriage 32 push the carriage 32 to the limit of its travel. The user feels a discontinuity in the movement of the lever as the rounded corner is moved over the surface of the carriage 32. There is thus a switching effect as the lever 31 moves from the locked to the unlocked position. This effect makes the switching operation of the lever 31 very easy to operate as it is in effect similar to a light switch moving from one position to the other.

The length of the lever 31 from the end which the user manipulates to the center of rotation of the pin 56 is substantially longer than the lengths from the surfaces in contact with the carriage 32 to the center of rotation of the pin 56. This configuration results in mechanical advantage for the user. The force which the user exerts on the lever 31 is amplified by the leverage of the lever 31 allowing the user to use less effort to lock and unlock the device.

The aliment of the feet 54 of the carriage 32 within the holes 53 of the body 30 is maintained by the walls of the body 30 which constrain the carriage 32 to remain within a confined pocket in the body 30. The clearance between the carriage 32 and the walls of the pocket in the body 30 is smaller than the clearance between the feet 54 of the carriage 32 and the holes 53 in the body 30. The feet 54 will thus always return to the holes 53 and never bind on the walls around the holes 53.

The carriage 32 is held in place by the floss 42 itself which in effect suspends the carriage 32. When the lever 31 is moved to the unlocked position and the user pulls on the floss 42 to advance the floss 42, the floss 42 exerts a pulling force on the carriage 32 and thus pops it into the unlocked position.

A compliant seal component 37 is installed in a cavity in the carriage 32. As the carriage 32 is moved into the locked position the seal covers the small passage 52 into the floss storage compartment and in fact the seal is compressed against the material around the small passage 52 as is shown in FIG. 12. The seal 37 prevents fluid from entering the floss storage compartment. The seal 37 is disengaged when the carriage 32 is moved to the unlocked position in order to facilitate movement of the floss 42 and to protect the seal from wear as the floss 42 is advanced.

This device was designed with a fluid management system Provisions have been made to prevent fluids such as water or saliva from remaining on the device for long periods. The floss storage compartment is sealed off on the top. Additionally, the cap 33 has ventilation ports 57 as shown on FIG. 5 to naturally ventilate the compartment. Four feet 49, 50 on the bottom of the cap 33 keep the device and the ventilation ports 57 off of the surface, such as a counter top, on which the device is placed. This prevents a puddle of water on this surface from blocking or wetting the ventilation ports. When the floss 42 leaves the storage compartment the floss 42 is routed through the device by a series of grooves 41. These grooves 41 are amply sized to expose the floss to the air and thus encourage the natural evaporation process to take place.

The aforementioned grooves 41 are positioned to always constrain the floss 42 to stay within the body 30. This is accomplished by alternating the side of the part to which the grooves 41 are exposed.

A sheet metal cutter 35 is used to cut off excess spent floss 42. Shown in FIGS. 20, 21 and 22, the cutter 35 is made from a piece of sheet metal with a punched and formed lip 58 in its center. The inner corners of the lip 58 are sharp enough to easily cut the floss 42. A hill 59 is formed around the lip 58 to prevent the user's hand from being cut while at the same time providing access for the floss. The edges 60 of the cutter 35 are folded over on two sides to conform to a track 61 on the body 30 which is shown on FIGS. 2 and 8. During assembly of the device the cutter 35 is slid along the track 61 until the cutter 35 hits the stop 62 on the body 30 at which time another folded side 64 of the cutter 35 snaps into a slot 63 in the body 30 and the cutter 35 is thus locked into place.

A threading device (not pictured) is used to thread the flossing tool during assembly and by the user in the event of floss breakage. The threader is a thin and somewhat flexible rod which is smaller in diameter than the width of the floss routing grooves 41 and longer than the length of the body 30. The bottom of the threader has a notch to which the floss 42 can be attached. The top of the floss storage cavity has a funnel like shape which guides the threader into the small passage 52. All of the holes 55 in the carriage 32 and all of the grooves 41 in the shaft 39 line up to form a continuous hole all the way through the part on both the floss 42 supply and on the floss 42 return sides. Thus, the threader need only be sent through the supply hole, around the U-shaped region 40 and back though the return side to fully thread the device. This procedure can be accomplished in a few seconds and need only be done during assembly or when the floss has broken. The locking mechanism itself should not break the floss, but occasionally the floss may be broken by rough teeth or dental work.

This device has been designed for mass production. The body 30, the lever 31, the carriage 32, the cap 33 and the spool rod 34 are all made of injection molded plastic. The sheet metal cutter is readily mass produced by stamping and forming. The compliant seal is also readily stamped out. The floss spool itself is commercially available. It should be noted that the drawings, for clarity, do not show the hollowing out of the plastic features required for the injection molding process.

We claim:

1. A dental floss holding device, comprising:
   (a) a handle;
   (b) a shaft extending from said handle, said shaft including means at one end for positioning dental floss near the teeth of a user;
   (c) floss gripping means for routing said floss through a tortuous path and holding said floss taught, said floss gripping means including first and second gripping members, said floss gripping means including rotatable locking means having a first locked position for continually holding said first and second gripping members in a position which establishes said tortuous path and holds said floss taught, said locking means having a second unlocked position for releasing said floss from said first and second gripping members;
   (d) said locking means including a lever and a pin, said pin positioned in a groove in said handle, said pin rotatably coupling said lever to said handle, said pin including stop means for limiting the degree of rotation of said lever.

2. A dental floss holding device as recited in claim 1, wherein said first gripping member includes a plurality of projections and wherein said second gripping member includes a plurality of openings, said projections mating with said openings.

3. A dental floss holding device as recited in claim 1, wherein said first gripping member includes a plurality of projections and wherein said second gripping member includes a plurality of depressions, said projections mating with said depressions.

4. A dental floss holding device as recited in claim 1, further comprising:
   (a) a floss holding compartment; and
   (b) compliant sealing means, associated with said locking means, for preventing fluids from entering said floss holding compartment when said locking means is in said first locked position.

5. A floss holding device, comprising:
 (a) a floss storage compartment;
 (b) active sealing means for protecting said floss storage compartment from fluids;
 (c) first ventilating means for ventilating said floss storage compartment, said first ventilating means including a plurality of air access ports;
 (d) a shaft extending from said floss storage compartment, said shaft including floss applying means at one end for applying floss to a user's teeth;
 (e) gripping means for holding said floss taught;
 (f) means for routing said floss from said storage compartment through said gripping means, through said shaft and through said floss applying means;
 (g) second ventilating means for providing air access passing through said gripping means;
 (h) third ventilating means for ventilating floss passing through said shaft, said third ventilating means including a plurality of alternating grooves positioned on opposite sides of said shaft; and
 (i) standoff means projecting from said floss storage compartment for holding said first ventilation means above a surface upon which said floss storage compartment is placed and preventing fluid on said surface from entering said first ventilation means.

* * * * *